(12) United States Patent
Salmon et al.

(10) Patent No.: US 8,160,694 B2
(45) Date of Patent: Apr. 17, 2012

(54) ADJUSTMENT MECHANISM FOR ELECTRICAL MEDICAL APPLIANCES, AND METHODS OF USE

(75) Inventors: Andrew Salmon, Auckland (NZ); Tak-Ming Chung, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1037 days.

(21) Appl. No.: 12/064,900

(22) PCT Filed: Aug. 28, 2006

(86) PCT No.: PCT/NZ2006/000216
§ 371 (c)(1),
(2), (4) Date: Apr. 15, 2008

(87) PCT Pub. No.: WO2007/024147
PCT Pub. Date: Mar. 1, 2007

(65) Prior Publication Data
US 2008/0234767 A1    Sep. 25, 2008

(30) Foreign Application Priority Data

Aug. 26, 2005 (NZ) .................................. 542081
Sep. 29, 2005 (NZ) .................................. 542755

(51) Int. Cl.
*A61N 1/00* (2006.01)
*G05B 13/00* (2006.01)
(52) U.S. Cl. .................................. 607/2; 700/11; 607/7
(58) Field of Classification Search ............... 607/2, 7, 607/36; 700/11, 12, 13, 17, 19
See application file for complete search history.

(56) References Cited

U.S. PATENT DOCUMENTS 5,558,084 A    9/1996 Daniell et al.
5,609,770 A *  3/1997 Zimmerman et al. ........ 210/739
5,830,151 A   11/1998 Hadzic et al.
(Continued)

FOREIGN PATENT DOCUMENTS
DE         26 40 961         3/1978
(Continued)

*Primary Examiner* — Carl H Layno
*Assistant Examiner* — Pamela M Bays
(74) *Attorney, Agent, or Firm* — Knobbe, Martens, Olson & Bear, LLP

(57) ABSTRACT

Electrical medical equipment that includes a user operable primary adjustment mechanism containing two or fewer user-adjustable elements, and a controller adapted to control and alter at least one output parameter of the equipment, the controller connected and responding to input from said primary adjustment mechanism to alter said output parameter, the primary adjustment mechanism having at least four conditions; a first condition which the mechanism returns to without user input, a second condition, following manipulation of one of the elements from a first condition, a third condition, following manipulation of one of the elements from a first condition, and a fourth condition following manipulation of the same element manipulated to achieve the third condition to another position, wherein in each condition, the mechanism provides a distinct output as input to the controller, which responds to the input by: maintaining the output parameter at a previous level while the input indicates the mechanism is in the first condition, incrementing or gradually increasing the prevailing level of the output parameter while the input indicates the mechanism is in the second condition, decrementing or gradually decreasing the prevailing level of the output parameter while the input indicates the mechanism is in the third condition, and setting the level of the output parameter to zero when the input indicates the mechanism is in the fourth condition.

26 Claims, 12 Drawing Sheets

U.S. PATENT DOCUMENTS

| | | |
|---|---|---|
| 6,393,325 B1 | 5/2002 | Mann et al. |
| 6,706,016 B2 | 3/2004 | Cory et al. |
| 6,719,780 B1 | 4/2004 | Salmon et al. |
| 2002/0065454 A1* | 5/2002 | Lebel et al. .................. 600/365 |
| 2003/0018395 A1* | 1/2003 | Crnkovich et al. ............ 700/11 |
| 2003/0139664 A1 | 7/2003 | Hunt et al. |
| 2006/0111756 A1 | 5/2006 | Chang |

FOREIGN PATENT DOCUMENTS

| | | |
|---|---|---|
| EP | 1 031 317 | 8/2000 |
| NL | 8800016 | 8/1989 |
| WO | 01/93953 | 12/2001 |

* cited by examiner

ADJUSTMENT MECHANISM FOR ELECTRICAL MEDICAL APPLIANCES, AND METHODS OF USE

This application is a National Phase filing of PCT/NZ2006/000216, having an International filing date of Aug. 28, 2006, which disclosure is herein incorporated by reference.

BACKGROUND OF THE INVENTION

1. Field of the Invention

The present invention relates to adjustment mechanisms for use in medical appliances.

2. Summary of the Prior Art

It is known to use electrically operated devices for a variety of purposes in medical applications. In these devices, it is desirable to be able to easily adjust, and if necessary, instantly zero, an output parameter such as current amplitude. A system for delivering heated humidified gases to a patient is disclosed in U.S. Pat. No. 5,558,084. In systems of this type, a switch, button, rotating knob or similar is included, which is used to adjust the level of heating or flow. The inventors have recognised a need for control systems on these devices which can be easily adjusted, and where the output current, or another output parameter, can be instantly zeroed if required. An operator of any of these devices would find it useful to be able to easily and instantly adjust the output via the adjustment switches, buttons or knobs on these devices, so that power or current, for example to the heater, the fan, or similar can be instantly zeroed. In particular, it would be desirable to instantly and easily zero the magnitude of the current amplitude, with no adjustment lag. One reason for the desirability of including a switch of this type is to avoid user discomfort caused by excessive flow pressure or excessively hot gases, or for example in order to avoid patient discomfort or tissue damage.

Another example of a device that may benefit from an instant zero is a radiant heater, such as the one described in U.S. Pat. No. 6,719,780. If a medical professional requires the power to be instantaneously shut off, or the current to be instantly zeroed, it would be useful for them to have access to a control device or switch that allows this.

Other medical devices that would benefit from including an instant zero include positive pressure breathing machines, and nerve stimulators. Outlined below are typical nerve stimulation operations and associated hardware, exemplifying why devices that include an instant zero are required.

In nerve stimulation and location, individual nerves or nerve bundles in a body are stimulated by application of an externally applied low-level electric current. This has several advantages in modern medical practice. For example, if the location of nerve bundles or nerve nexuses in a body is accurately known, these can be avoided during invasive surgery, decreasing the chances of damage to the nerves of a patient. A further advantage is in general or local anaesthesia, where nerve stimulation techniques can be used to locate the best site for the injection of local anaesthetic, to judge an appropriate amount of anaesthetic, or to judge the level of anaesthesia of a patient.

Nerve stimulation is carried out by applying an electric current to a location on the body of a patient, usually close to a nerve nexus. The reaction of the body part (twitch response) is observed as the current amplitude, current pulse frequency, and (in some operations) the location of a current carrying electrode are altered. In this manner, nerve locations or an anaesthesia level, or both, can be judged.

There are several specialist nerve stimulator devices currently on the market, for use in operating rooms or similar, which can deliver low-level electric current for nerve stimulation or detection. Normally, these devices are battery-powered, and are sized so as to fit the palm of a users hand. A typical device is the 'Innervator NS272', as manufactured by the applicant and shown in FIG. 1. Probes or electrodes suitable for delivering a low-level current to a user are connected to the nerve stimulator via connected leads. An example of these combination leads and electrodes is shown in FIG. 2a. In some applications, such as nerve location, a user may prefer to use a combination drug administration needle and electrode. An example of this type of combination is described in U.S. Pat. No. 6,706,016. The electrode/needle is used to locate a nerve or nerve nexus close to an area where local anaesthetic is required, with anaesthetic delivered directly to the area via the needle.

Alternatively, a user may prefer to use a double-headed shrouded diagnostic probe, similar to the one manufactured by the applicant, and shown in FIG. 2b. This connects directly to the output of the nerve stimulator, and is brought into contact with the patient where required.

In most nerve stimulators, the current output and other useful information is displayed to a user on a display screen. A user holds the nerve stimulator in one hand, and observes output readings such as current amplitude on the display, while using their free hand to locate an electrode in or on a user.

It is common practice to detachably mount the nerve stimulator on a bracket, pole or similar, so that a user has both hands free to manipulate electrodes or other equipment, while still easily observing output readings.

Usually, nerve stimulators are operated in one of two main modes, a first mode where the device is used for nerve location, and a second mode where the device is used for nerve stimulation.

The nerve location mode is used when nerve locations need to be accurately mapped, for example so that these locations can be avoided when carrying out invasive surgery around that area. Nerve location is also used in local anaesthesia, when it is desired to administer the anaesthetic drug as close to a nerve as possible, without the drug administration needle touching the nerve.

The general process that is usually followed for nerve location can be outlined as follows:

Nerve locations in the human body are known approximately, with the exact locations varying from individual to individual. In order to accurately locate nerves on a patient, a first sensor/electrode is attached close to a known nerve location, by taping the sensor to their skin, or similar. The initial location of this first electrode is normally judged 'by eye'. A second electrode (or electrode/needle combination) is also connected to the nerve stimulator. An operator touches the second electrode to the skin of the patient, close to the first sensor. If the second electrode is an electrode/needle combination, the tip of the needle is usually inserted into the muscle, close to a nerve or nerve nexus location. The current from the nerve stimulator fires nearby nerves and causes the associated muscles to contract, or twitch. The nerve stimulator current can be pulsed, e.g. at a frequency of 1 Hz, in order to help an operator observe the 'twitch response'. Depending on observations of the 'twitch response', an operator can judge the nerve location and administer drugs appropriately.

It is usual practice to commence a nerve location search with a current amplitude of between 0.6 mA and 2 mA. The exact value will depend on the preference of the individual practitioner. However, the starting current amplitude is usually kept low, with the operator or user judging the initial twitch response and increasing the current amplitude if necessary. Starting the operation at a low current level helps avoid patient discomfort, and reduces the possibility of damage to a patients nerves. If no twitch response is observed at a low current output, the current amplitude is increased until a response is observed. The location of the nerve relative to the electrode can be judged, and the electrode or needle moved closer to the nerve, with the current amplitude and pulse frequency adjusted until the nerve location mapping is completed. It is considered good practice to reduce the current amplitude as the electrode is moved closer to the nerve, in order to avoid discomfort or damage. The pulse frequency can be increased to compensate for the reduced current amplitude, so that the twitch response remains observable. If the current level is reduced to approximately 0.2 mA, and muscle twitches are still observable, then the needle is known to be approximately 2 mm from the nerve. If using a needle/electrode combination, an anaesthesia drug can be directly administered at this location.

Nerve stimulation methodology is normally used when a patient is or will be under general anaesthesia (fully paralysed). In nerve stimulation, the aim is to find the supramaximal current. This is the current level that causes all nerve fibres in a bundle to fire at the same time, and is usually between 4 OmA and 5 OmA for most humans. If the supramaximal current is known, appropriate doses of anaesthetic can be administered. Also, post-anaesthesia administration, if a current is applied at the supramaximal level, and no response is observed, this is a reliable indication that the anaesthesia is working correctly.

There are two main methods which are normally used for finding the supramaximal current value for an individual. These are outlined below.

In the first method (pre-anaesthesia), current is applied to the body in a similar manner to that outlined above for nerve location, starting at a low initial current amplitude value (usually the lowest possible value the nerve stimulation unit is capable of). The current amplitude is gradually increased to the point where a twitch response is just observable. The supramaximal current amplitude for the individual is three times this level.

In the second method (post-anaesthesia), the patient is anaesthetised before any nerve stimulation is carried out. Nerve stimulation is carried out, until the maximum twitch response is observed (that is, the point at which increasing the current amplitude no longer increases the size of the twitch response). The supramaximal current value is 120-130% of the amplitude of this current level.

Several devices exist that can be used for nerve stimulation and location. Devices also exist which can be used to measure the twitch response in a more accurate fashion than can be achieved with simple observation 'by eye'.

The applicants 'Innervator™' range can be used to carry out the operations described above. An example, the 'Innervator NS272', is shown in FIG. 1. The current amplitude and other parameters are controlled by means of standard buttons on the upper surface. Standard in this context should be taken as meaning that the buttons are inactive until depressed. The buttons have one depressed position, and when depressed, will activate or carry out one pre-set or hardwired function.

The controls of the NS232 model also include a button pair, one of the pair used to increase current amplitude in incremental steps when depressed, and the other used to decrease current amplitude in incremental steps.

One problem that can occur when carrying out nerve stimulation in the manners described above is patient discomfort or, in some cases, nerve damage. As nerves are extremely sensitive to electric current, minor changes in the position of a current-carrying electrode or needle close to a nerve can cause discomfort or damage. This can occur even when an operator is paying due care and attention, and carrying out location and stimulation methodology in accordance with best practice. With some existing nerve stimulators it is also possible, through human error or carelessness, to touch an electrode to the body with the current amplitude set to a high or maximum value, and the unit turned on. If the electrode is initially applied with a high current output, close to a nerve, this can cause discomfort or damage. In some situations it can be difficult to immediately remove an electrode from contact, for example if a needle/electrode combination is being used, and care would need to be taken to remove the needle. It may also be the case that removal of an electrode from contact with the body at that moment is undesirable, for example if an electrode/needle is suitably located for administration of anaesthesia. It is therefore useful for an operator to be able to rapidly or instantaneously decrease the current output to zero.

Life-tech, Inc. manufacture a nerve stimulator and locator, which offers a similar functionality to the 'Innervator™' range. The Life-tech. Inc. 'Tracer® III', shown in FIG. 4, has a central knob, which a user rotates clockwise or anticlockwise to adjust the amplitude of the current. In order to ascertain with any precision what the current amplitude value is (i.e. the exact position of the knob), the unit must first be switched on.

Another product which uses a central knob to control the amplitude of the current is the 'Stimuplex® HNS11' manufactured by B Braun, shown in FIG. 3a, and in use in FIG. 3b. The central control knob of the 'Stimuplex® HNS11' acts as an on/off switch. Rotating the knob to the furthest anticlockwise position turns the unit off.

Nerve stimulators that use central knobs offer a responsive and easily adjustable current output. However, if the central knob is used as the main current control mechanism, it needs to be rotated through a range of movement (i.e. from the use position, to zero), in order to zero the current output.

The 'Tracer® III' offers the additional functionality of a pause button, which is said to cut the current flow to an attached electrode. This pause button is located remotely from the central knob. An operator using both hands to adjust the unit can keep one on the control knob, and one on the pause button, making adjustments to the current amplitude as required. If necessary, the operator can depress the pause button and zero the current output. An operator using both hands in this manner may find it difficult to make adjustments to the position of an electrode. If an operator is using one hand to adjust the electrode position, and the other to alter the current, they will need to move their hand from the control knob in order to reach the pause button. Similarly, if an operator is holding the unit in one hand, (or if it is supported on a stand), with one hand being used to make adjustments to the current amplitude, and the other being used to position an electrode, an operator will need to move their hand from the control knob, over to the pause button in order to cut the current output.

Several other control mechanisms for nerve stimulator devices are available which can be used to minimise user discomfort, and increase ease of use for an operator. U.S. Pat. No. 6,706,016 describes an electrode and anaesthesia needle combination, where the current control switch is located on the electrode. The electrode/needle combination is connected to a remotely located nerve stimulator. The switch allows an operator to alter the current, using the same hand they are using to change the location of the electrode/needle.

In U.S. Pat. No. 5,830,151, the current amplitude from the nerve stimulator is controlled by means of a connected and remotely located foot pedal, which is depressed by a user in order to increase the current. When the operator removes their foot from the pedal, the current remains at a constant amplitude.

One other output that a user may wish to easily adjust or trigger is current pulses at pre-programmed amplitudes and pulse frequencies. A user may also wish to quickly and easily change the current amplitude or pulse frequency if these need adjusting after a user has commenced use. It can be seen that there is an identified need for devices that enable a user to make these adjustments easily and via conveniently located controls.

The inventors have recognised a need for medical devices including nerve stimulators where the current amplitude and other outputs are easily adjustable. An operator would therefore find it useful to have access to a medical device such as a nerve stimulator where all the controls are easily accessible and easily adjusted, for example by using one hand or one digit (e.g. the thumb of the hand holding the nerve stimulator), and where the number of sub-operations or manipulations to the controls required when in use is kept to a minimum. The inventors have particularly determined that it would be desirable to be able to instantly and easily drop the magnitude of the current amplitude from a nerve stimulator to zero with no adjustment lag, in order to avoid patient discomfort or nerve damage

SUMMARY OF THE INVENTION

It is an object of the invention to provide a nerve stimulation device which goes some way towards overcoming the difficulties outlined above, or which will at least provide the public with a useful choice.

Accordingly the present invention may broadly be said to consist in electrical medical equipment, including;

a user operable primary adjustment mechanism containing two or fewer user-adjustable elements, a controller adapted to control and alter at least one output parameter of said equipment, said controller connected and responding to input from said primary adjustment mechanism to alter said output parameter, said primary adjustment mechanism having at least four conditions;

a first condition which the mechanism returns to without user input, a second condition, following manipulation of one of said elements from said first condition, a third condition, following manipulation of one of said elements from said first condition, and a fourth condition following manipulation of the same said element manipulated to achieve said third condition to another position, wherein in each said condition said mechanism provides a distinct output as input to said controller, said controller responding to said input by:

maintaining said output parameter at a previous level while said input indicates said mechanism is in said first condition, incrementing or gradually increasing the prevailing level of said output parameter while said input indicates said mechanism is in said second condition, decrementing or gradually decreasing the prevailing level of said output parameter while said input indicates said mechanism is in said third condition, and setting the level of said output parameter to zero when said input indicates said mechanism is in said fourth condition.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

FIG. 2b shows a probe that can be plugged into the prior art nerve stimulator in place of the leads and probes of FIG. 2a.

Figure 1:
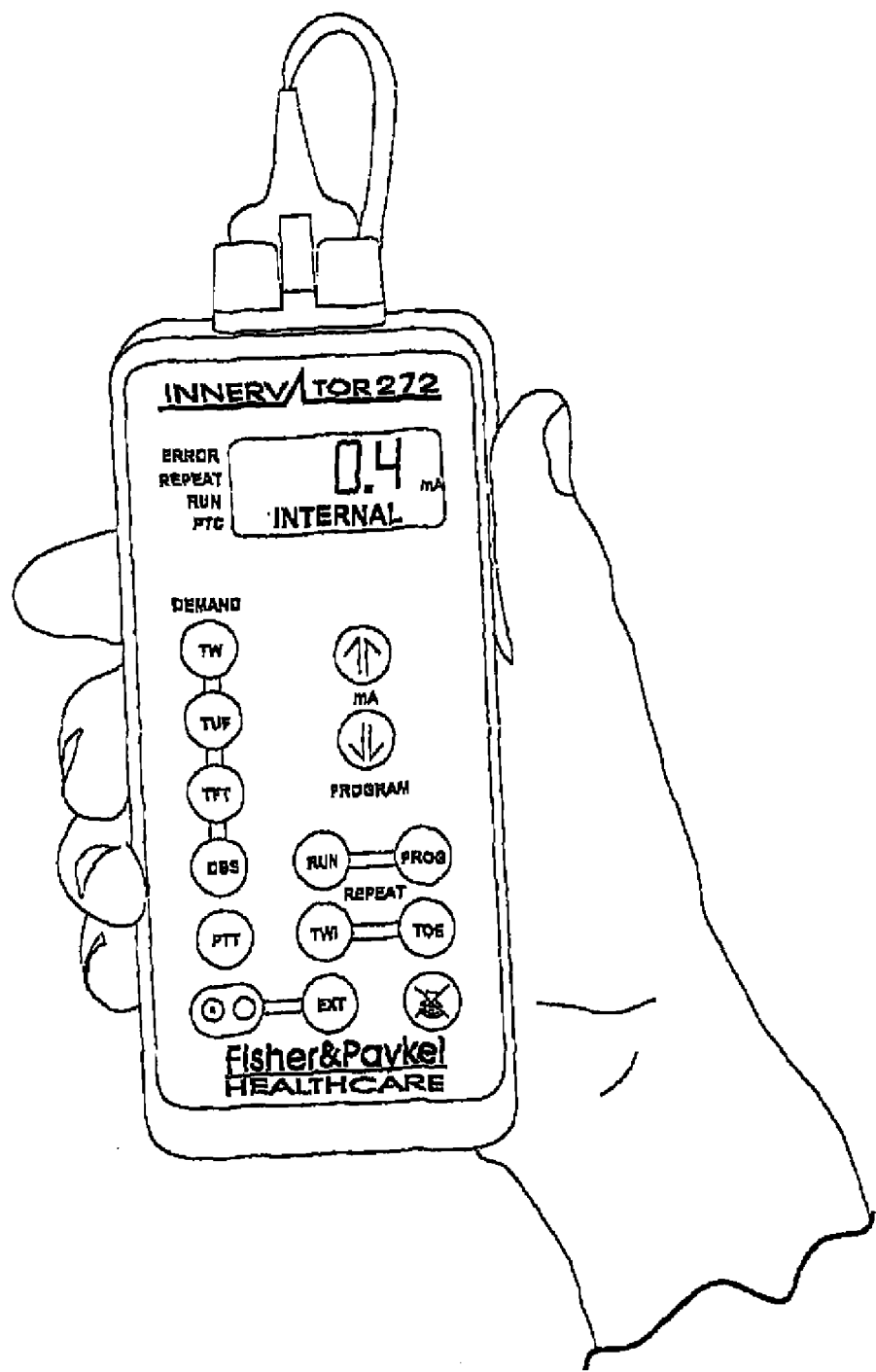
FIG. 1 shows a typical prior art nerve stimulator, as manufactured by the applicant.

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

DETAILED DESCRIPTION OF THE PREFERRED EMBODIMENTS

Disclosed is a parameter adjustment mechanism for electrical medical equipment, which is described with particular reference to a nerve stimulation device, or nerve stimulator 1. It should be noted that the adjustment mechanism described can be used for a variety of other uses in medical equipment, such as humidifiers, radiant heaters, positive pressure breathing assistance machines, or similar. It should also be noted that a variety of adjustment mechanisms are described, such as button pairs, rotating knobs, etc. For convenience, all the different types of controls, e.g. button pairs, rocker switches, rotating knobs and 4-way switches, will be referred to as 'adjustment mechanisms' throughout this specification where an overall term is required.

The nerve stimulation device described can be used at least in nerve location (also referred to as internal mode), or nerve stimulation (also referred to as external mode).

Figure 5:
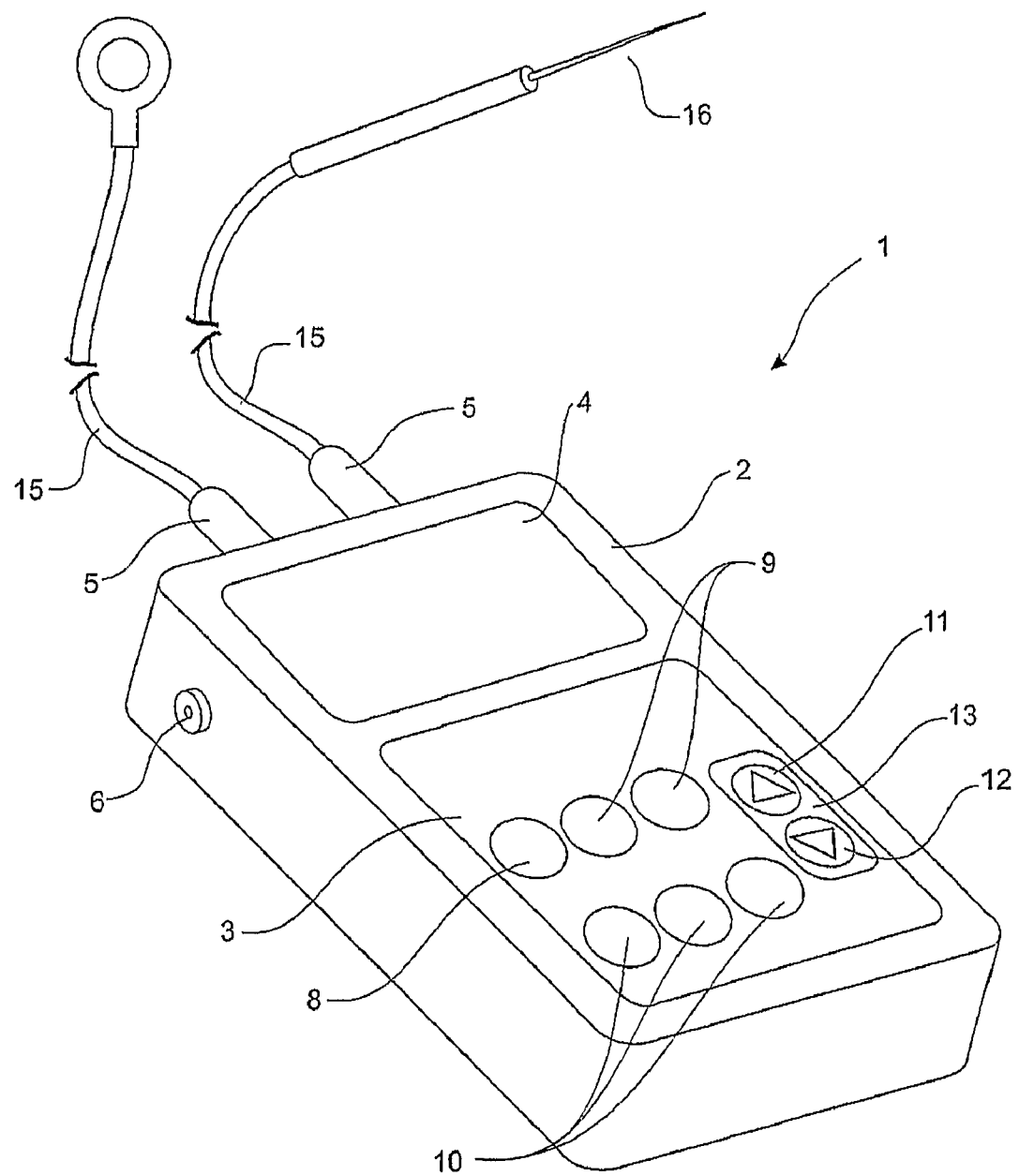
FIG. 5 shows the nerve stimulator of the present invention, and in particular the control and display layout.

A preferred embodiment of the parameter adjustment mechanism of the present invention is shown in use with a nerve stimulator 1 in FIG. 5. The nerve stimulator 1 has a rectangular box shape, and is sized to be held comfortably in the palm of a users hand. When held in a users hand ready for use, the upper or top face 2 of the nerve stimulator 1 includes user controls 3 and an output display 4.

Figure 7:
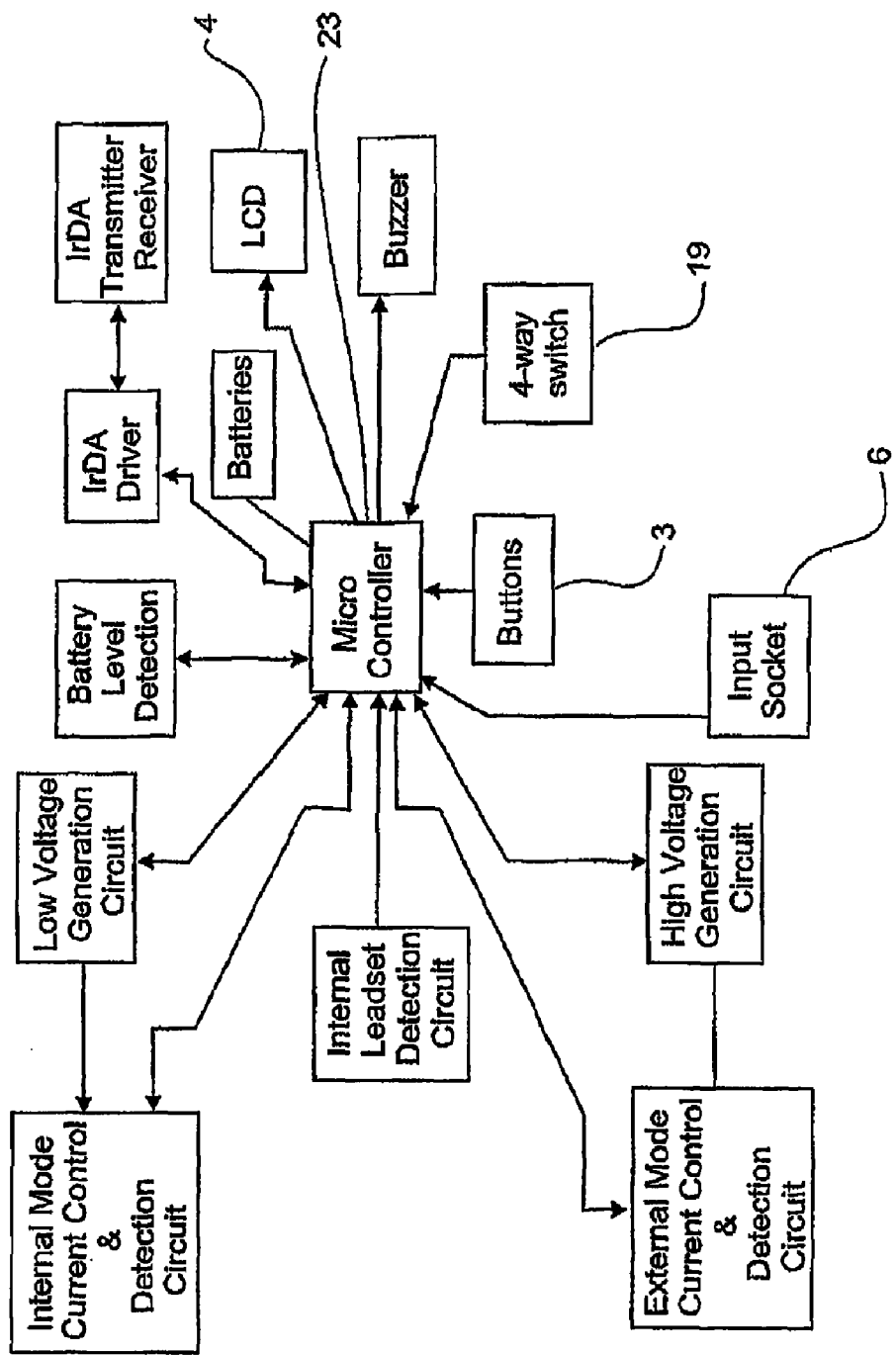
FIG. 7 shows a block diagram of the internal circuitry and power supply of the nerve stimulator of the present invention.

In the preferred embodiment, the nerve stimulator 1 is built around a micro controller 23, as shown in the block diagram of FIG. 7. The micro controller 23 and the associated auxiliary parts are contained within a casing that has external apertures for buttons and sockets, as shown in FIG. 5, and can be generally referred to as an integral hardware means.

Figure 2A:
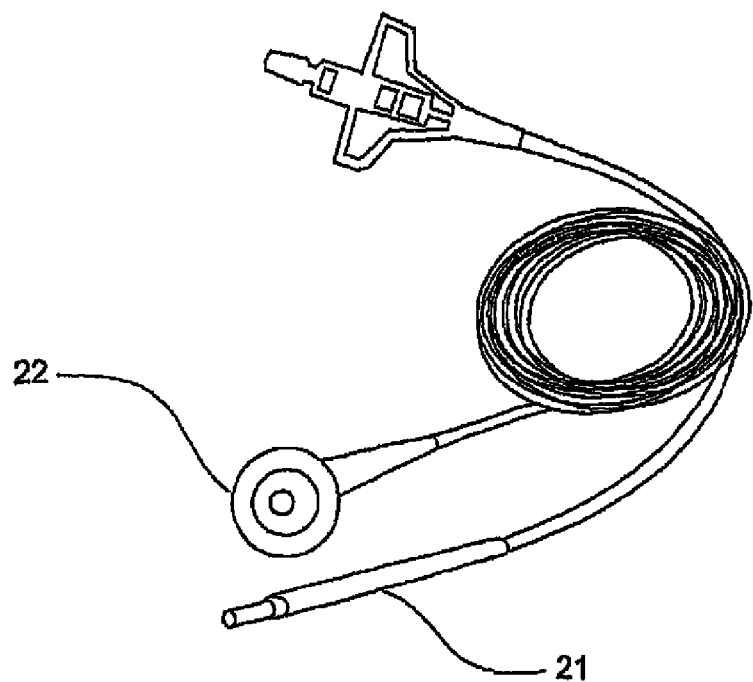
FIG. 2a shows a set of leads and probes suitable for use with the prior art nerve stimulator of FIG. 1.

The nerve stimulator 1 includes a set of sockets 5 for connecting electrodes 15 to the nerve stimulator 1. For example, these electrodes might be of the type shown in FIG. 2a. The sockets 5 also allow alternative tools, such as a diagnostic electrode similar to the one shown in FIG. 2b to be connected to the output of the nerve stimulator 1. The preferred embodiment of the nerve stimulator 1 also includes at least one input socket 6 to allow connection to a remote source such as a computer (not shown). This connection allows routines that have been previously composed on the computer to be downloaded and added to a simple memory contained in the circuitry (hardware means) of the nerve stimulator 1, or allowing the routines to be run directly from the computer via the nerve stimulator 1. Also, in some situations, a user may wish to remotely control a nerve stimulator from another location, for example via the computer.

In the preferred embodiment, the display 4 is of the LCD type. The display 4 can be adjusted to show a range of information. Generally, medical professionals who would be using the device, such as anesthetists and doctors, prefer to see the current output in milliamps (mA) as part of the main display. Ancillary information, such as a current pulse rate, current pulse width, or output wave type (square wave current output, sine wave current output, etc) can also be shown.

The nerve stimulator 1 has controls 3, including a parameter adjustment mechanism. In the preferred embodiment, the controls 3 are all buttons built into the body of the nerve stimulator 1. Buttons, switches, or knobs that stand proud of a surface can be difficult to clean effectively, and microbial build-up can occur. The controls 3 in the preferred embodiment are covered by a continuous and flexible membrane which forms the upper face 2, and which is marked with the positions and functions of the buttons underneath, so that they can be activated by pressing on the appropriate part. A continuous surface has the advantage of being easy to wipe clean and sterilise.

The controls 3 of the nerve stimulator 1 include an on/off switch or button 8, and buttons 9. The buttons 9 can be set by a user (by pre-programming the hardware means) to act as trigger buttons, triggering current pulses or pre-set routines. In the preferred embodiment, the buttons 9 also include a frequency adjustment button, for altering the pulse frequency (e.g. between 1 Hz and 2 Hz), and a width adjustment button, for altering the pulse width (also called pulse duration). In a single transition pulse, the pulse width/duration will be the time the pulse takes to go from a specific low point, to a high point, and back to the specific low point again. In a multiple transition pulse, the pulse width (or duration) will be the interval between the time point during the first transition where the pulse amplitude reaches a specified fraction (level) of the final amplitude, and the time point on the final transition of the pulse at which the pulse amplitude drops to the same level. The controls 3 also include program buttons 10, which allow the microprocessor or hardware means of the nerve stimulator 1 to be pre-programmed with simple routines that can be activated using the buttons 9. The controls 3 could also include buttons (not shown) to change the display output. It is preferred that the nerve stimulator 1 is programmed such that when the activated by means of the on/off button 8, the current output will have a default value of zero.

The controls 3 of the nerve stimulator 1 also include the adjustment mechanism of the present invention. In the preferred embodiment, this is an up/down switch pair 13, comprising an up button 11 and a down button 12. However, any suitable type of adjustment mechanism can be substituted for the button pair 13. Buttons 11 and 12 are co-located, so that a user can change quickly from increasing a parameter to decreasing a parameter with minimum effort, for example by moving their finger or thumb a short distance from one button to the other. The button pair 13 is preferably located towards one side of the nerve stimulator 1, so that the buttons 11 and 12 can be reached and operated by the thumb of a user holding the nerve stimulator 1 in the palm of their hand. However, the button pair 13 can be located anywhere on the nerve stimulator 1 that is convenient for a user. This leaves the other hand free to carry out other operations, such as changing the location of an electrode.

In the preferred embodiment of the present invention, each of up button 11 and down button 12 are dual-pressure buttons. A first function is activated by pressing the button to a first or intermediate position. For example, this first function could be increasing the current by one pre-set increment. When the button is fully depressed to a second position, a second function is activated. This could be an immediate increase to a pre-set maximum current, with no intervening ramp-up steps. The buttons 11, 12 can be used to change the output current level directly in use, or to set a preferred current level, the output current activated at that level by pressing another button.

It should be understood that although a button pair 13 has been described, controls with similar functionality could be used, such as a rocker switch with a default neutral central position, and positions each side of the central neutral set depending on the users preference. For example, the rocker switch could have first and second up positions, and first and second down positions. Alternatively, a rocker switch with four possible positions could be used, a neutral position, one up position and two down positions. Depressing the rocker switch towards the casing in which the switch is located could act as the instant zero (that is, pushing the whole of the switch towards the casing).

Alternatively, a rotating knob located either on the top surface, or on the side of the nerve stimulator 1, could be used to adjust the current. Instead of a second position, the rotating knob could be depressed, acting as a button (that is, pushed towards the casing). If a rocker switch or a rotating knob is used, these will have a neutral position where no change to an output parameter is occurring. This would be the equivalent of neither of the buttons 11, 12 being depressed. In the preferred embodiment, the neutral position would be the central position of a rocker switch, with at least one and preferably two up positions, and a first and second down position, each side of the neutral position. The rocker switch would be biased to return to the neutral position if no pressure was exerted in either direction. The output parameter would instantly zero if the rocker switch was pressed into the second down position.

For a rotating knob, the neutral position could be either when the knob is not rotating or being rotated either clockwise or anticlockwise. That is, a first direction or a second direction. For this setup, the knob would automatically be 'biased' towards a neutral position, which would occur when the knob is not being rotated. Alternatively, a rotating knob that is biased to automatically return to a neutral (e.g. central) position could be used, with the adjustment rate of a parameter related to how far from the neutral position the knob is rotated away. That is, the rate of change of a parameter would depend on how far the knob is rotated away from a neutral position. If the rotating knob was depressed, the output parameter would instantly zero.

A three-position rocker switch could also be used, with a central neutral position, and an up and down position each side of this neutral position. Depressing the entire rocker switch into the casing or a recess (as opposed to 'rocking' it) would instantly zero the parameter.

Figure 6:
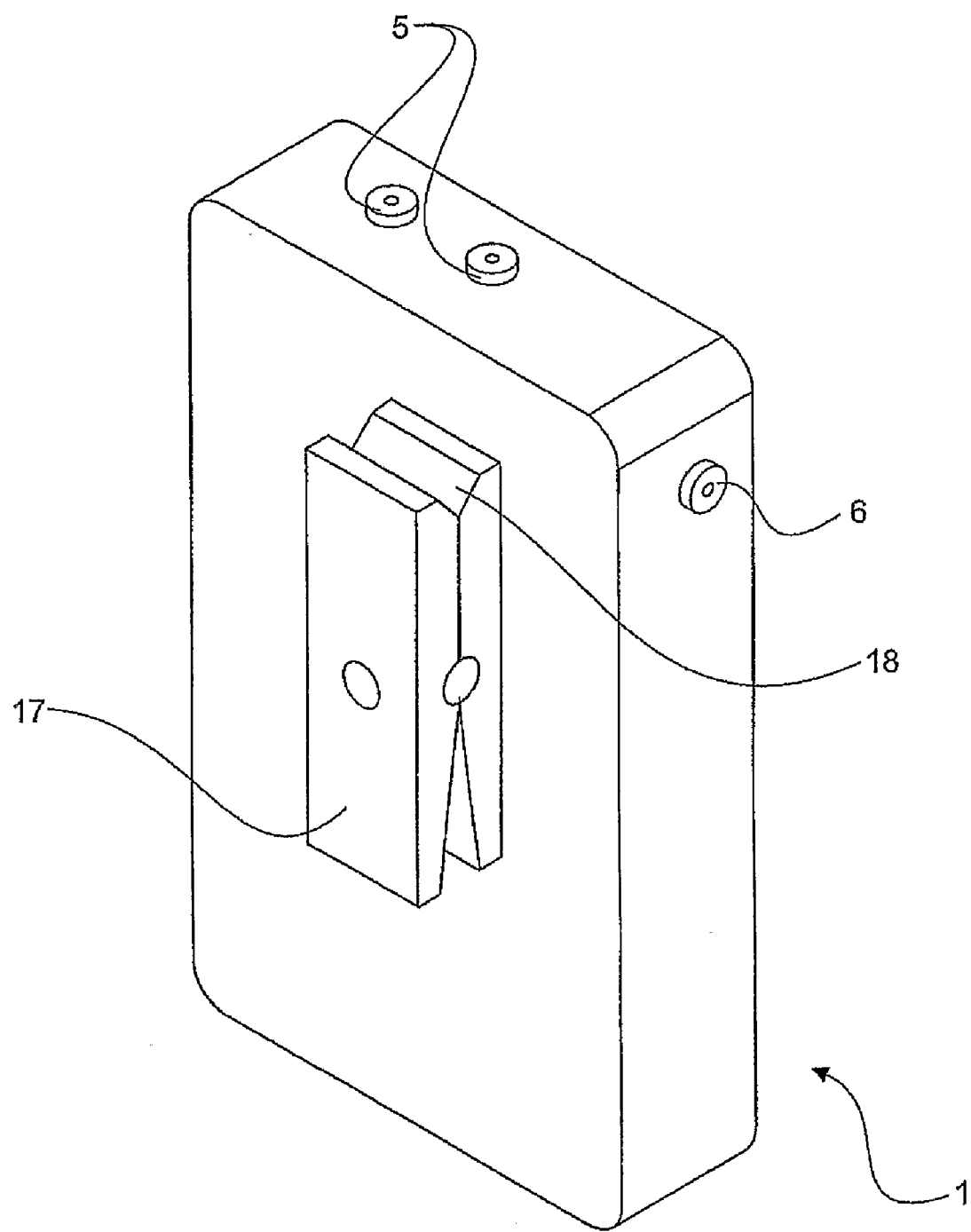
FIG. 6 shows the nerve stimulator of the present invention with a spring clip attached to the rear face, aligned for upwards engagement.

One further feature of the nerve stimulator 1 of the present invention that adds to the ease of use is shown in FIG. 6. A peg or spring clip 17 is connected to the rear face of the nerve stimulator 1. The spring clip 17 allows the nerve stimulator 1 to be clipped to, or hung from e.g. surgical curtains or drapes in an operating theatre, the smock of an operator, or any other convenient item. The spring clip 17 is biased to the closed position, and can be opened with the same hand that is holding the nerve stimulator. If required, a notch 18 can be added to the jaws of the spring clip, at the front opening, so that the spring clip can be pushed into engagement with an item without having to first open the jaws. The most useful alignment of the spring clip 17 is with the jaws opening facing upwards, so that the unit can be hung from a curtain or similar. However, in the preferred embodiment, the central attachment mechanism (e.g. a screw or bolt), could be temporarily loosened to allow the spring clip to be swiveled to any position a user requires.

Preferred embodiments of the functionality that could be attributed to the controls 3 is outlined below, although further programmable functionality beyond what is specifically described is of course possible.

The main functions of the preferred embodiment of the nerve stimulator 1 are nerve location (internal mode) and nerve stimulation (external mode).

In the preferred embodiment, the default function of the up/down button pair 13 is to change the amplitude of the output current, this being the parameter that a doctor or an anesthetist will most frequently wish to adjust. The incremental increases or decreases of the current value for each press of the buttons 11, 12 to a first position are either pre-set to a default level (for example, increments of 1 mA, 2 mA etc), or programmed by a user. This programming would either be via the controls 3, or via a remote connection to a PC.

It is also preferred that the controls include a button that will increase the pulse frequency by 1 Hz every time the button is pressed, up to a value of 3 Hz. A subsequent press of the button will cause the pulse frequency to revert to zero. That is, repeatedly pressing the button will cause the pulse frequency to vary as follows: 0 Hz-1 Hz-2 Hz-3 Hz-0 Hz etc. Due to the fully programmable nature of the controls, the maximum value of 3 Hz can easily be altered, to 4 Hz, 5 Hz, or whatever value is required by the operator.

The procedure followed for the two main operations (stimulation and location) has been generally described in the prior art section above, but will now be described in more detail, specifically with reference to the operation of nerve stimulator 1 of the present invention, and the benefits therein.

Nerve Location, or Internal Mode & Programmable Pulse Mode

A generally preferred starting value of the current amplitude for nerve location has not been well-defined in the medical art, and depends largely on the preference of the individual. A typical starting value could for example be anywhere from 0.6 mA to 2 mA.

The nerve stimulator 1 is turned on, with the current level at the default zero level. A preset current amplitude is chosen by a first touch or press of one of the buttons 9. A second touch of either the same or a different button activates the current flow at this pre-set level. This level is adjusted as necessary by means of the up/down button pair 13. Depressing the up button 11 to the first position increases the current amplitude in pre-set increments. The default value of these increments would be for example 0.5 mA. However, these could be adjusted to an individual users preference via the controls 3. Similarly, a user pushes the down button 12 to a first position to reduce the current incrementally.

For both first positions of the up button 11 and the down button 12 outlined above, the buttons have "press and hold" functionality. Each single press of the button to a first position increases or decreases the current by one increment. If a user presses and keeps the button depressed, the nerve stimulator 1 will either ramp up or ramp down the current as appropriate, for as long as the button is kept depressed. In the preferred embodiment, the current increases to 80 mA when the button is depressed and held. In order to increase the current beyond 80 mA, a user must repeatedly press and release the button, in order to increase the current in incremental steps.

When the up button 11 is pressed to the second position, the current amplitude is immediately increased to a pre-set maximum value. This functionality allows anesthetists or doctors to immediately set the current to their preferred initial level with one convenient button press.

The operation of the dual-pressure switch of the present invention will now be described with particular reference to the operation of the nerve stimulator 1.

The second position of the down button 12 acts as an 'instant zero'. If the current amplitude is too high, too close to a nerve, this can cause user discomfort or nerve damage. In order to either instantly zero the current level, or instantly shut off the actual current flow to the electrode or needle (depending on a pre-programmed preference), the down button 11 is depressed to the second position.

It would also be possible to use a rotating knob in place of, or with, the button pair 13, as the adjustment mechanism. The knob would be rotated clockwise and anticlockwise to adjust a parameter such as current. The equivalent of depressing the up button 11 to a first position to increase a parameter would be rotating the knob in one direction (e.g. clockwise). The equivalent of pressing the down button 12 to a first position would be rotating the knob in the other direction (e.g. anticlockwise).

In order to instantly zero the current, a user would press the rotating knob inwards, the knob acting as a button when pressed. In particular, pressing the knob inwards would have the same effect as depressing down button 12 to the second position. That is, instant zero. The knob could be located wherever is most convenient for a user, for example, on the top surface of the nerve stimulator 1, or on the side. If required, the knob could be made so that the further away from a neutral position it is rotated, the faster the parameter selected (e.g. current) is adjusted.

Figure 9:
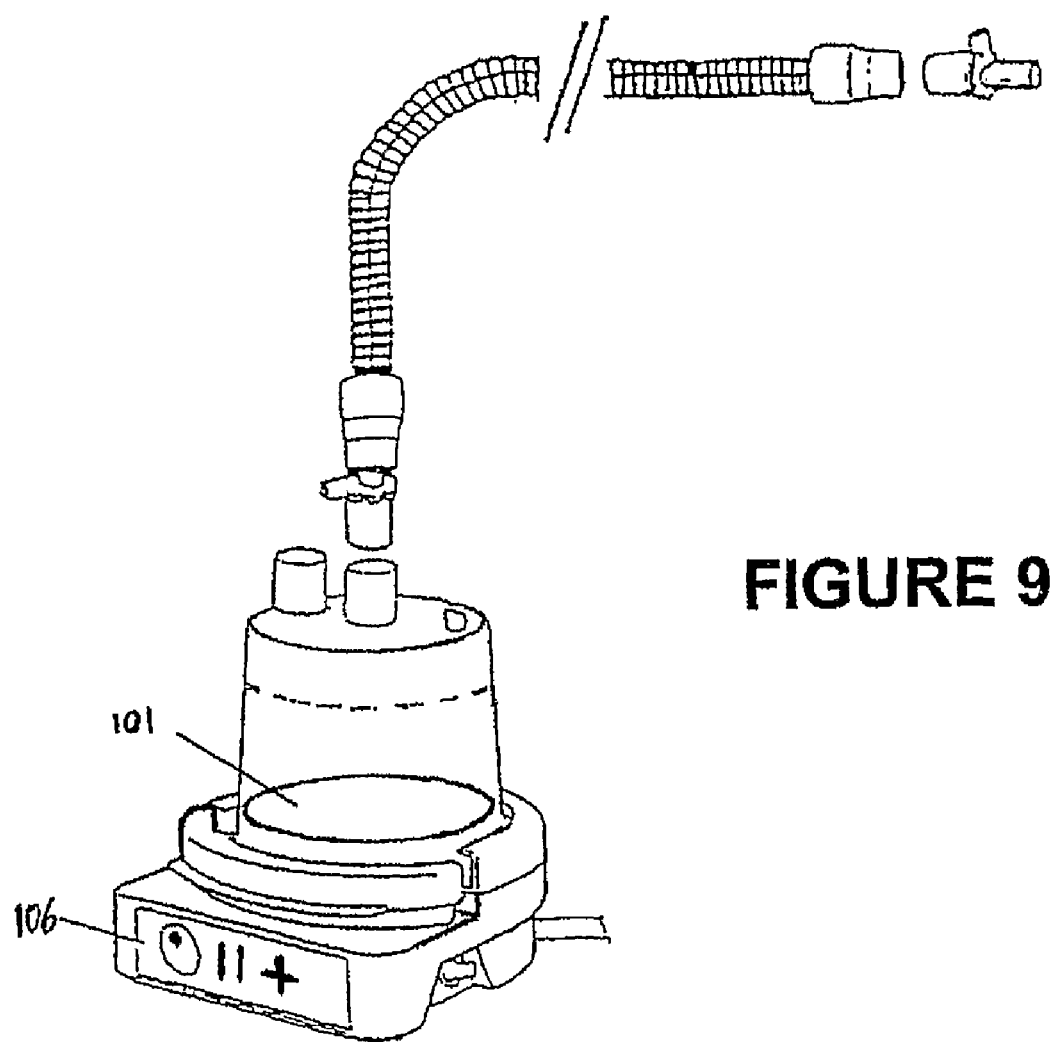
FIG. 9 shows a humidification system for supplying heated humidified gases to a patient, such as could be used with the switch of the present invention.
Figure 10:
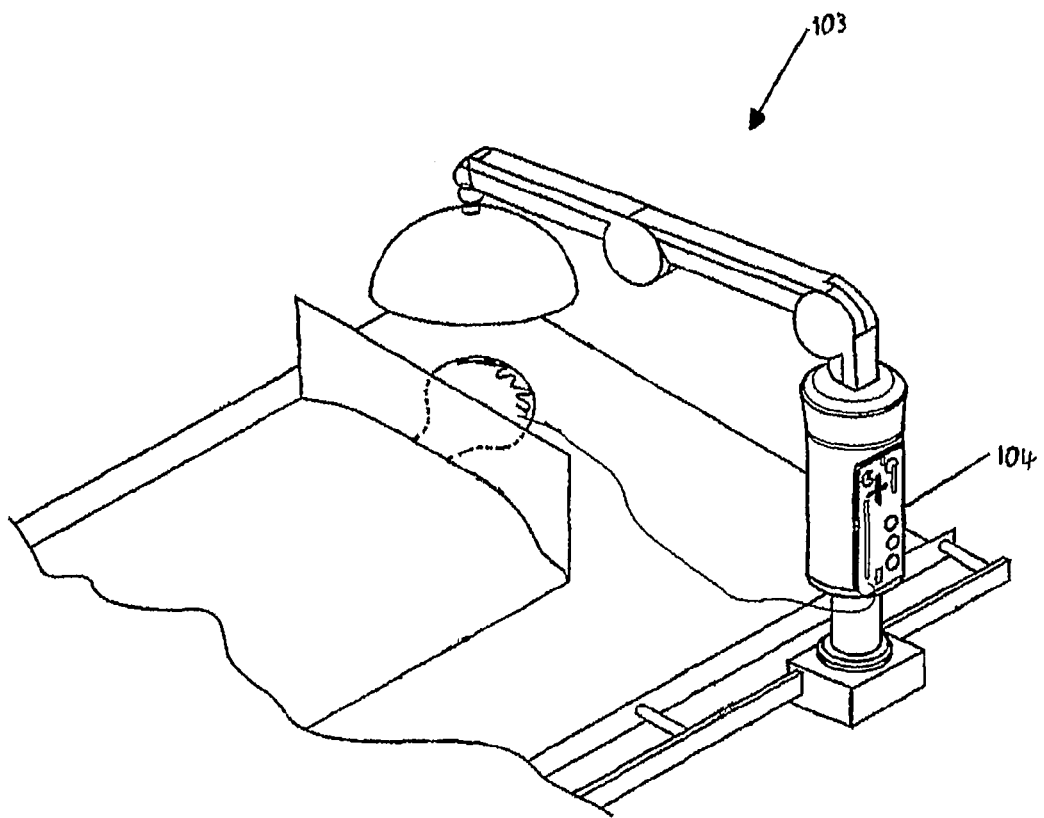
FIG. 10 shows a radiant warming device, such as could be used with the switch of the present invention.
Figure 11:
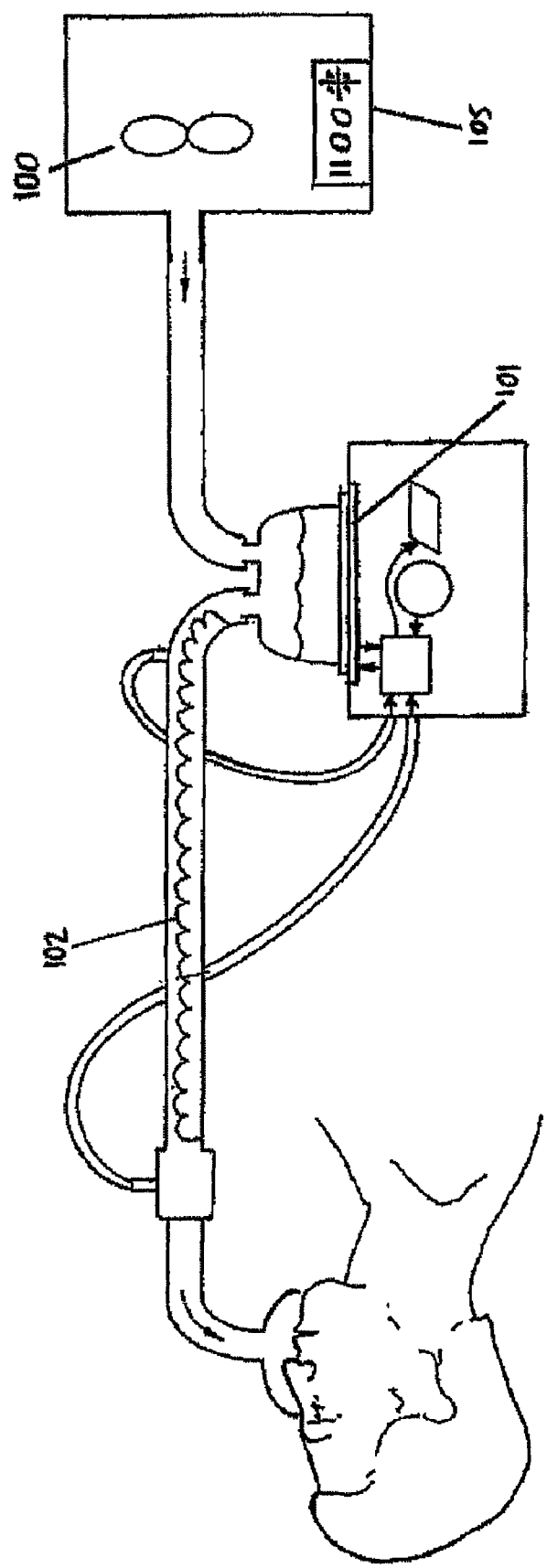
FIG. 11 shows a positive pressure breathing assistance machine such as could be used with the switch of the present invention.

This instant zero also has advantages in other medical devices or procedures. For example, in the operation of positive pressure breathing assistance machines similar to the one shown in FIG. 11, a system or device to supply humidified gases to a user similar to the one shown in FIG. 9, or a radiant heater similar to the one shown in FIG. 10. For all of these devices, it is desirable to be able to instantly zero one or more parameters, in order to avoid patient discomfort or tissue damage. For example, it is desirable to be able to instantly zero the current to the fan 100 shown in the device of FIG. 11. It would also be desirable to instantly zero the current that powers the heater plate 101 or heated conduit 102, or the current to a radiant warming device 103. It should of course be understood that other parameters other than current could be instantly zeroed by means of the mechanism described. An example would be in the operation of the radiant heater 103. An operator could instantly zero an output parameter, such as the current to the bulb, element, or other radiant heating means, using the adjustment mechanism of the present invention located in the control panel 104, in order to minimise patient discomfort or the possibility of damage, or simply as a more convenient mechanism for a user. Similarly, a user could instantly zero the current or other output parameters via the adjustment mechanism of the present invention, in the control panels 105, 106 of the devices shown in FIGS. 9 and 11.

It should of course be understood that any other suitable mechanism, such as those described above, could also be used in place of the rotating knob or switch pair described above.

In the nerve stimulator embodiment, the button pair 13 can be either set to increase/decrease the actual current (that is, the actual current output at the electrodes), or the proposed current (that is, the current that will output on activation—the actual current), the amplitude shown on the display while under adjustment, but the actual current output being zero. For safety reasons, 'instant zero' always zeros the actual current.

When using the nerve stimulator 1 for nerve location, it is preferred that the current is pulsed in order to aid observation of the twitch response and help locate the nerve or nerve nexus. It is usual practice to start with a pulse frequency of 1 Hz. In use, as the electrode is moved closer to the nerve location, the current level is reduced to avoid patient discomfort, and the pulse frequency is increased in order to aid continued observation of the twitch response at lower current amplitudes.

In the preferred embodiment, one of the buttons 9 adjusts the frequency. The default frequency on activation of the nerve stimulator 1 is 0 Hz. One press of the button increases the pulse frequency to 1 Hz, with subsequent presses increasing it in 1 Hz increments, to 2 Hz, 3 Hz etc. It is preferred that this current frequency adjustment button is located close to, or co-located with, the dual-pressure switch pair 13, so that it can be easily reached using the same digit that is used to adjust the current amplitude.

The nerve stimulator 1 can be programmed to run pre-set current, frequency, and pulse width routines in use, the different steps of which can be easily triggered by a user, for example by pressing one of the buttons 9. These routines allow variations in the current amplitude, pulse frequency, and/or pulse width, tailored to the requirements or preferences of an individual user. Several different routines are known and commonly used in the art, including: Single Twitch (SW), Train of Four (TOF), Double-Burst Stimulation (DBS), Tetanic Stimulation (TET), and Post-Tetanic Count (PTC). Set templates for these routines are programmed into the memory of the nerve stimulator 1, with default values of current amplitude and frequency that can be adjusted by a user if required. Alternatively, fully user-customised routines can be programmed and stored in the memory.

In the preferred embodiment, the nerve stimulator 1 is programmed with preset double-burst stimulation routines. Double-burst stimulation usually includes two rapid bursts of three pulses, with a 750 ms interval between the two rapid bursts. Usually, the three pulses are separated by a 20 ms interval, creating one rapid burst. It has been found that it would be useful for an operator of a nerve stimulator to be able to vary these parameters if required. Therefore, in the preferred embodiment, the nerve stimulator 1 is pre-programmed with two variations on this routine that can be easily accessed by an operator. In the first of these variations, the first rapid burst is three pulses, with a second rapid burst of two pulses following after a 750 ms interval. In the second of these variations, the first rapid burst is two pulses, with a rapid burst of three pulses following after a 750 ms interval. These preset routines are accessible directly from the memory of the nerve stimulator 1. However, in the preferred embodiment, it is possible for a user to vary the parameters of the routines. i.e. the number of pulses in either of the rapid bursts can be altered, the 750 ms interval can be increased or decreased, and the 20 ms interval between the pulses in the rapid bursts can be adjusted, if required.

For example, the controls can be programmed to increase pulse frequency and decrease current amplitude by pre-set increments each time a pre-set one of the buttons 9 button is pressed. A pre-programmed routine, with a current amplitude of 5 mA, and a pulse frequency of 1 Hz, is triggered by pushing a designated one of the buttons 9. For each subsequent button press, the current amplitude decreases by 0.5 mA, until an output value of 0.4 mA is reached. At this point, with each subsequent button press, the pulse frequency automatically increases by 1 Hz, and the current amplitude decreases by 0.1 mA, down to a minimum value of 0.2 in A.

Alternatively, two or more buttons 9 could be pre-programmed, one increasing the pulse frequency by a pre-set amount, and one decreasing the current by a pre-set amount for each press. This flexibility and pre-programmed functionality allows a user to concentrate their attention on patient comfort and the location of the electrode and nerve(s), while still easily adjusting the output parameters of the nerve stimulator 1.

These custom routines are pre-programmed into the nerve stimulator using the controls 3. Alternatively, these routines can be pre-programmed on a PC using appropriate software, and downloaded into the memory of the nerve stimulator 1 by connection via input socket 6. It should be noted that all of the adjustment and programming described above as taking place via the controls 3, could also be carried out via the remote connection via input socket 6, to a computer.

Nerve Stimulation, or External Mode

When operating in nerve stimulation, or external mode, the electrodes are in contact with the skin of the patient, and the risk of damaging a nerve or causing a patient extreme discomfort, is consequently not as great as when electrodes are inserted under the skin. When operating a unit in nerve stimulation mode to find the supramaximal current for an individual, an operator will usually start with a current amplitude lower than the average value, increasing this in use if necessary. It is therefore preferred when operating in this mode that the unit can be activated easily, with an appropriate starting current level easily set, or a pre-set program easily activated, with the current amplitude adjusted easily in use.

The functionality of the adjustment mechanism, e.g. the up button 11 and the down button 12, is the same as outlined above, with step increments, or ramp up/down. Fully depressing the up button 11 to the second position sets the current to a pre-set level. Fully depressing the down button 12 instantly zeros the output current. It should be noted that pre-programming the functionality of the buttons via the controls 3, or a remote connection via port 6 to a computer, is the same for external mode as has already been outlined for internal mode. It should also be noted that a rotating knob, or rocker switch, or any other mechanism as described above, could be used in place of the button pair 11, 12 described.

Being able to store and use custom pulse and current patterns has advantages when using the nerve detector 1 in external mode. These are outlined below.

As has been outlined above, there are two main methods for finding the supramaximal current for an individual: either 1) observing the current level which just causes a twitch response in an unconscious patient, or 2) increasing the current amplitude until the twitch response reaches a maximum. An accelerometer or a low-frequency phonomyographic microphone, positioned appropriately on the patient, is used to measure the size of the twitch response. The use of both of these devices for measuring twitch response is well-known.

The nerve stimulator 1 is run in programmable pulse mode. The size of the twitch response is measured on delivery of the current pulse, and this measurement fed back into the nerve stimulator 1. The nerve stimulator 1 is started with a current amplitude of e.g. 20 mA, automatically step-increasing this current amplitude with time. For example, the current amplitude is increased by 10 mA every 5 seconds. The twitch response is measured with each current pulse. When the size of the twitch response does not increase with a step increase in current amplitude, then the supramaximal current value must lie within the range of the second-to-last step-increase (for example, between a step-increase of 40 mA and 50 mA). The nerve stimulator 1 then automatically increases and decreases the current amplitude in small increments between these values, measuring the twitch response each time and comparing this with the previously measured maximum twitch response, increasing or decreasing the current based on the result of this comparison. In this manner, the current amplitude that causes the maximum twitch response can be found.

The rate and size of the step increases can be pre-set to a users personal preferences, and the program triggered by one push of one of the buttons 9. As above, if it is required to drop the amplitude of the current to zero for any reason, this can be achieved instantly by fully depressing the down button 12 to the second position.

It can be seen that for the methods described above, it is useful for a medical practitioner, or user of the nerve stimulator, to be able to easily adjust output settings while concentrating on nerve location and user comfort. A further embodiment that increases this functionality and usability shall now be described.

4-Way Switch

A further type of adjustment mechanism that users may find useful is described below, with particular reference to use with the nerve stimulator 1. It should of course be noted that this mechanism can be used for other devices, such as a positive pressure breathing assistance machines, humidification system or radiant heater, for example.

One operation that a medical professional may carry out using a nerve stimulator such as nerve stimulator 1 is positioning an e.g. anesthetic needle close to a nerve. It may be useful for them to be able to adjust current characteristics such as amplitude and frequency using the same hand that they are using to position the needle, rather than adjusting these characteristics using their other hand, which would be positioned on a remotely located nerve stimulator.

Figure 2B:
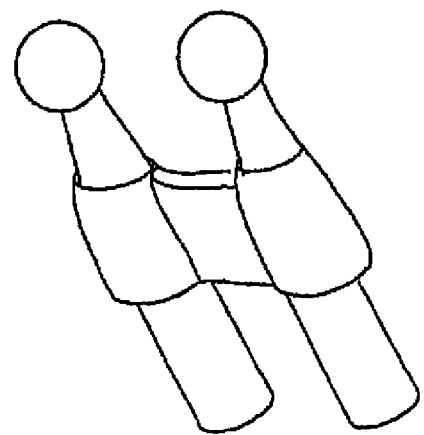
Figure 3A:
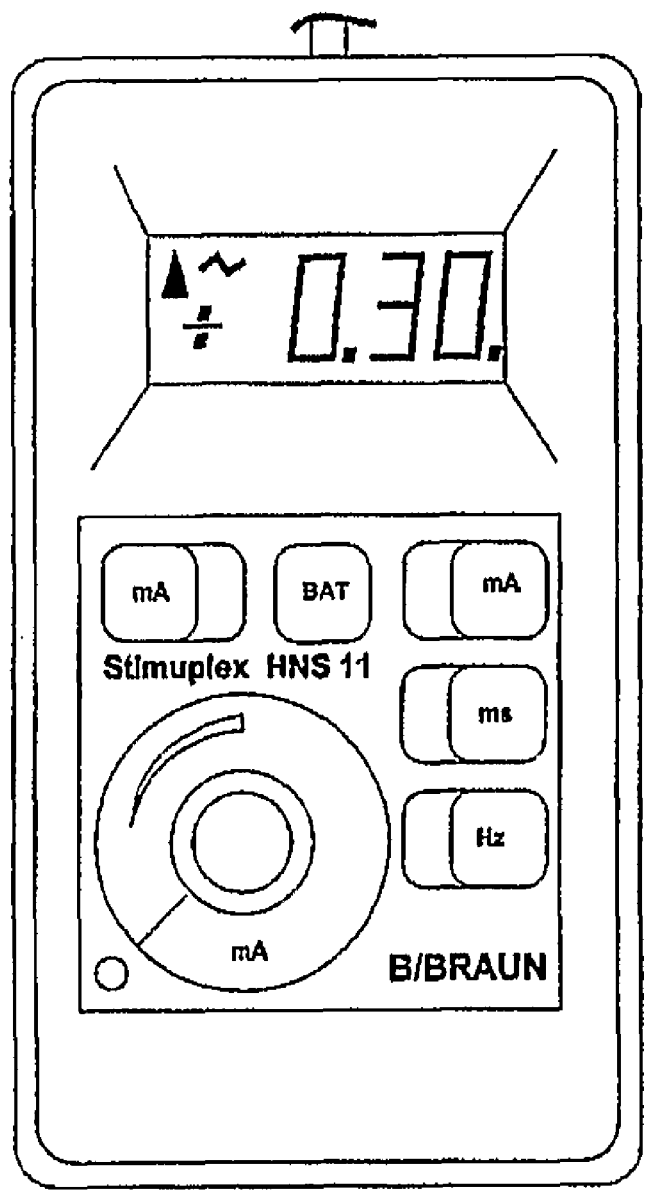
FIG. 3a shows a prior art nerve stimulator manufactured by B Braun, with output current controlled by means of a central rotating knob, rotated fully counter-clockwise to turn the unit off.
Figure 3B:
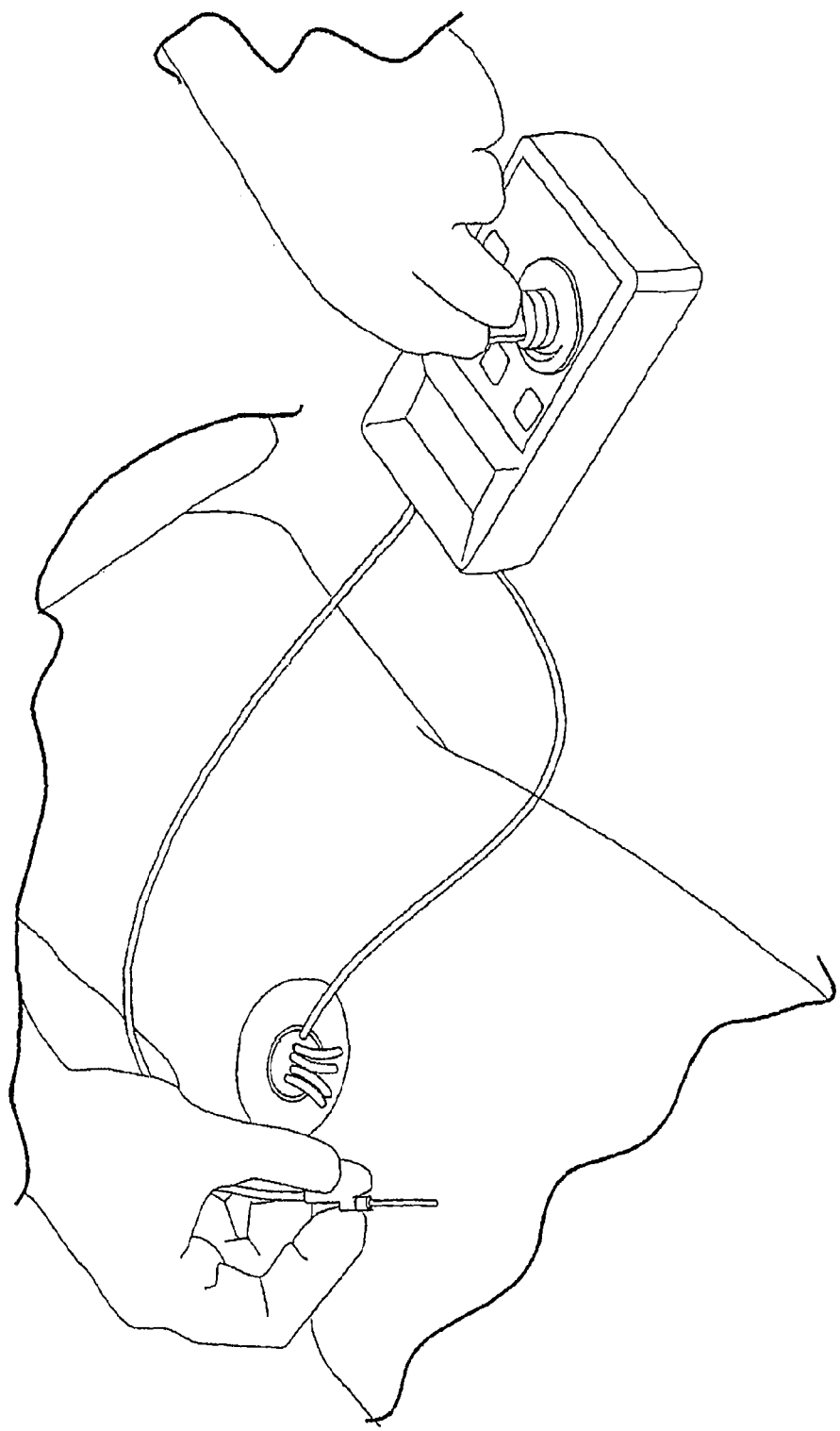
FIG. 3b shows the prior art nerve stimulator of FIG. 3a in use.
Figure 4:
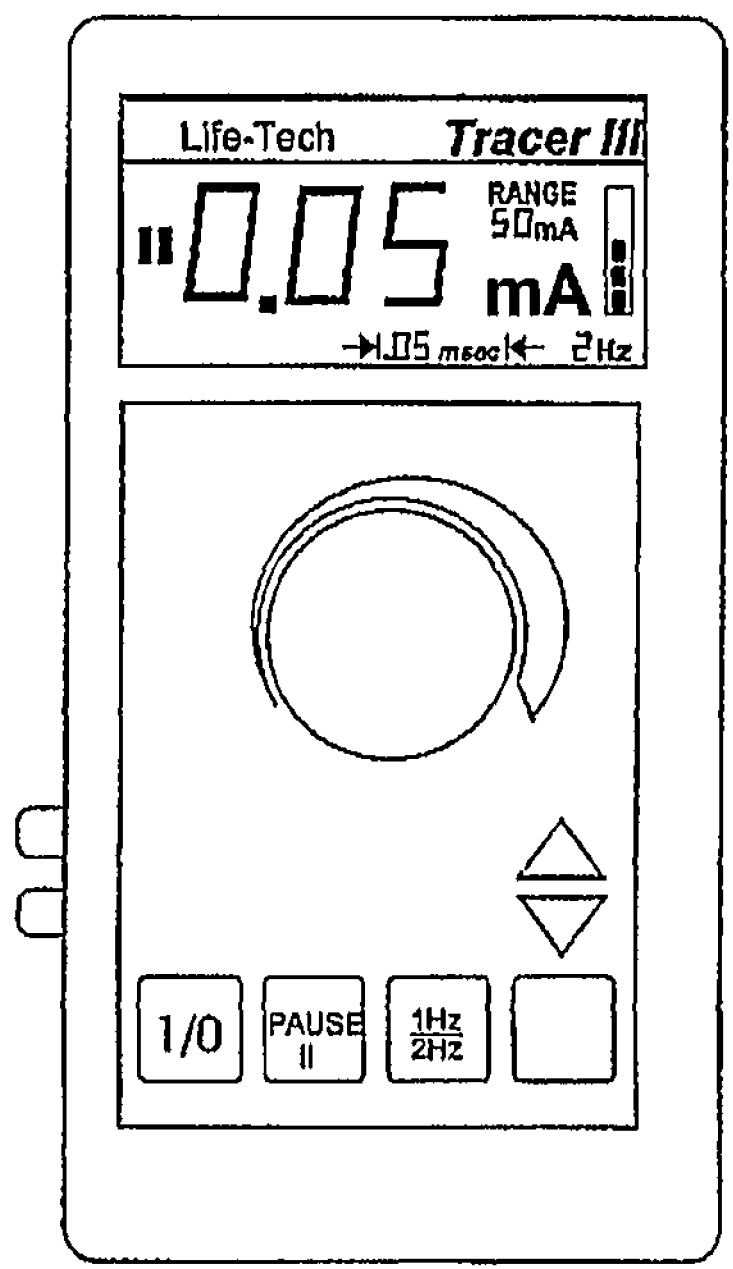
FIG. 4 shows a prior art nerve stimulator manufactured by Life-Tech, inc, with output current controlled by means of a central rotating knob and a pause button.
Figure 8:
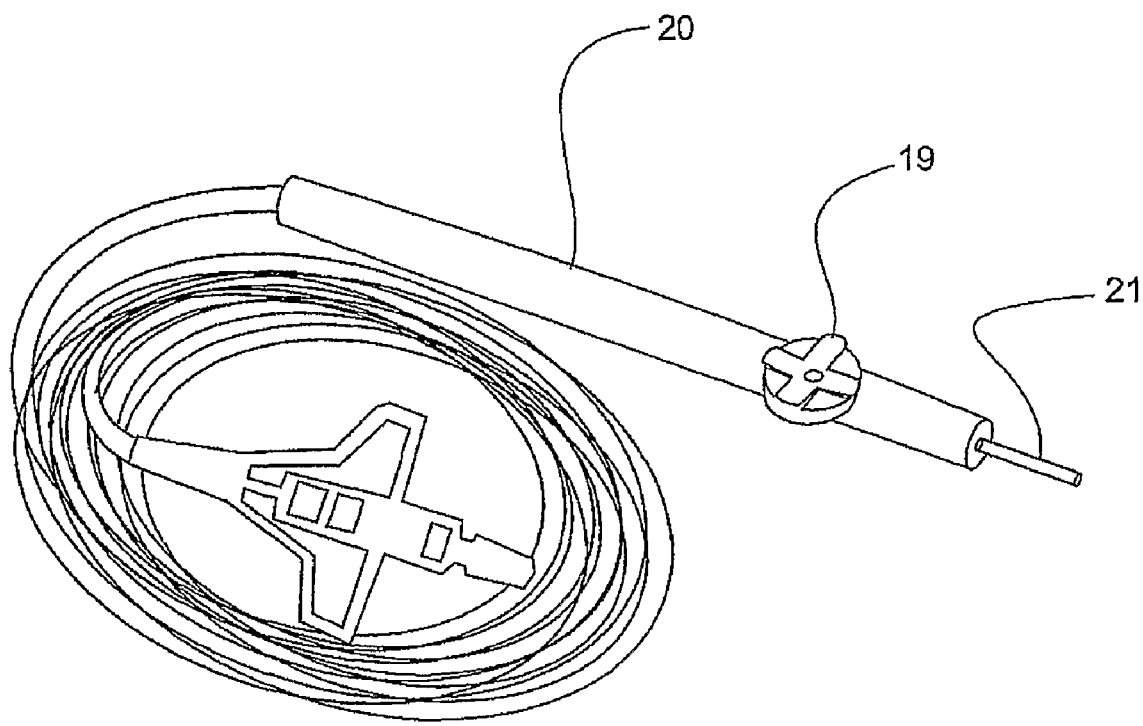
FIG. 8 shows a 4-way switch located on the housing of a nerve stimulation needle, the switch used as a controller for the output current characteristics of the nerve stimulator of FIG. 5.

As shown in FIG. 2b, it is usual for lead sets of the type that are commonly used with nerve stimulators to have one lead terminating in a cap 22 that fits over an pre-positioned electrode on a patient, with the other lead terminating in a pin 21, which in use attaches to, or is co-located with, an anesthetic administration needle. The pin 21 is manipulated by an anesthetist/doctor, and is used to locate a nerve or nexus for drug administration, in a similar manner to that already described above. In a variation of the invention described above, and as shown in FIG. 8, a 4-way switch 19 is located on a grip/housing 20 connected to the pin 21. In the preferred embodiment, the switch 19 is a 4-way rocker switch, similar to that used in e.g. mobile phones or computer game controllers. A user adjusts current amplitude by rocking the switch 'up' and 'down' (or 'backwards' and 'forwards'). Current frequency is adjusted by rocking the switch from side to side, or left and right. However, if preferred, two switches can be used, one to adjust current frequency, and one to adjust current amplitude. Any other suitable control combination can also be used. It should be noted that the instant zero functionality of the adjustment mechanism (e.g. the ability to instantly zero the current by pressing the button to a second position) can also be used with the 4-way switch 19 described above.

In summary, the adjustment mechanism described above, in use with the nerve stimulator 1, offers at least the following advantages:

Firstly, it is not possible to switch a device on, with current immediately flowing, which potentially could cause discomfort to a user.

Secondly, a device such as nerve stimulator 1 that includes an adjustment device as described above (such as a button, switch, or knob that has an 'instant zero') has the advantage that an operator can instantly stop the current flow by means of a conveniently located button, even when both hands are engaged, for example in electrode position adjustment and current amplitude adjustment. A user does not need to move their hand to another part of the control panel, and there is no lag such as might be associated with a rotating knob. As noted above, adjustment mechanisms such as the dual-pressure or dual-position button described, or the knob/button combination, can also be used on other electrical medical equipment. For example, systems or devices for delivering humidified gases to a user, radiant heating devices, etc.

Thirdly, an operator can pre-programme settings or routines to their personal preferences, with these routines easily triggered and then adjusted in use, allowing an operator to concentrate on actions such as nerve location, nerve stimulation, and patient comfort.

Fourthly, the nerve stimulator 1 described above has fully programmable parameters, which can be adjusted and programmed by means of the controls 3, or remotely, via port 6. This allows an operator to fully customise a routine and e.g. the amplitude, frequency and pulse width of the output for a given situation or patient, in order to achieve the best result.

The invention claimed is:

1. Electrical medical equipment, including;
   a user operable primary adjustment mechanism containing two or fewer user-adjustable elements,
   a controller adapted to control and alter at least one output parameter of said equipment, said controller connected and responding to input from said primary adjustment mechanism to alter said output parameter,
   said primary adjustment mechanism having at least four conditions;

a first condition which the mechanism returns to without user input, a second condition, following manipulation of one of said elements from said first condition, a third condition, following manipulation of one of said elements from said first condition, and a fourth condition following manipulation of the same said element manipulated to achieve said third condition to another position, wherein in each said condition said mechanism provides a distinct output as input to said controller, said controller responding to said input by:

maintaining said output parameter at a previous level while said input indicates said mechanism is in said first condition, incrementing or gradually increasing the prevailing level of said output parameter while said input indicates said mechanism is in said second condition, decrementing or gradually decreasing the prevailing level of said output parameter while said input indicates said mechanism is in said third condition, and setting the level of said output parameter to zero when said input indicates said mechanism is in said fourth condition.

2. Electrical medical equipment as claimed in claim 1 wherein said primary adjustment mechanism is a switch pair, said switch pair comprising an up button and a down button, said up button having at least one depressed position, said down button having at least two depressed positions, an intermediate depressed position and a fully depressed position, and wherein said first condition corresponds to a state when said buttons are not depressed, said up button in a depressed state corresponds to said second condition, said down button depressed to an intermediate position corresponds to said third condition, and said down button fully depressed corresponds to said fourth condition.

3. Electrical medical equipment as claimed in claim 1 wherein said primary adjustment mechanism is a rocker switch having a plurality of positions which correspond to said conditions, said rocker switch biased towards a first position corresponding to said first condition, said rocker switch manipulable by a user to a position corresponding to said fourth condition.

4. Electrical medical equipment as claimed in claim 3 wherein said first position is the central position of said rocker switch, said rocker switch having at least one up position corresponding to said second condition, an intermediate down position corresponding to said third condition, and a fully depressed down position corresponding to said fourth condition.

5. Electrical medical equipment as claimed in claim 4 wherein said equipment is a system for delivering humidified gases to a patient.

6. Electrical medical equipment as claimed in claim 4 wherein said equipment is a system for providing radiant heat energy to a patient.

7. Electrical medical equipment as claimed in claim 4 wherein said equipment is a positive pressure breathing assistance machine.

8. Electrical medical equipment as claimed in claim 4 herein said equipment is a nerve stimulator.

9. Electrical medical equipment as claimed in claim 8 wherein said nerve stimulator is capable of providing a current output parameter that is variable in any one, or all of amplitude, frequency, and pulse width, and wherein the default parameter increased or decreased by using said primary adjustment mechanism is current amplitude, said controller being a microprocessor programmed to ensure that said actual current output will always be zero on initial activation of said nerve stimulator and that the default current frequency on activation of said nerve stimulator is 0 Hz, said nerve stimulator further including a display adapted to show at least said amplitude of said actual current from said nerve stimulator.

10. Electrical medical equipment as claimed in claim 9 wherein said primary adjustment mechanism forms part of a set of controls for said nerve stimulator, said controls also including a separate on/off button or switch for activation and deactivation of said nerve stimulator, a current frequency adjustment button for adjusting the frequency of said current output via said controller, said primary adjustment mechanism located on said nerve stimulator such that a user can both hold said stimulator in one hand and operate said adjustment mechanism with said one hand.

11. Electrical medical equipment as claimed in claimed in claim 10 wherein said controller is programmed such that depression of said frequency adjustment button increases the current pulse frequency in 1 Hz incremental steps and wherein said controller is programmed such that once said current pulse frequency reaches a pre-programmed or default maximum, the first subsequent depression of said current frequency adjustment button will reset said current pulse frequency to 0 Hz.

12. Electrical medical equipment as claimed in claim 11 wherein said current frequency adjustment button is co-located with said primary adjustment mechanism, such that said current frequency adjustment button can also be operated with said one hand in use, said set of controls further including a pulse width adjustment button adapted to adjust the frequency of said current output via said controller.

13. Electrical medical equipment as claimed in claim 12 wherein said display is also adapted to show the amplitude of a display current, said display current adjustable separately from said actual current, said amplitude of said actual current unchanged until said display current is activated, said nerve stimulator further adapted such that said amplitude of said display current can be adjusted separately from said actual current via said controller by manipulation of said primary adjustment mechanism.

14. Electrical medical equipment as claimed in claim 13 wherein said controller includes a memory, said memory capable of storing at least user preferred current amplitude levels, such that accessing said memory by using said controls immediately shows said amplitude of said display current at said user preferred level.

15. Electrical medical equipment as claimed in claim 14 wherein said controls also include at least one programmable trigger button, a user able to program said controller with pre-set routines of pre-set current amplitude, frequency, and pulse width which run once said trigger button is pressed, and wherein a user can adjust the size of said current increments by programming said controller via said controls.

16. Electrical medical equipment as claimed in claim 15 wherein said nerve simulator also includes an input mechanism, said input mechanism allowing said controller to be remotely connected to a computer, and wherein said user-preferred current amplitude levels and said routines of pre-set current amplitude, frequency, and pulse width are in sue downloaded to said controller via said remote connection.

17. Electrical medical equipment as claimed in claim 16 wherein said double-burst stimulation is in the form of a first set of a variable number of rapid pulses and a second set of a variable number of rapid pulses, separated by a pause of a variable time interval, said variable pulse numbers and said variable time interval programmed into said controller via said computer and said remote connection.

18. Electrical medical equipment as claimed in claim 16 wherein said remote connection allows said nerve stimulator to be controlled remotely from said computer.

19. Electrical medical equipment as claimed in claim 15 wherein controller is pre-loaded with routines of pre-set current amplitude, frequency and pulse width, said routines including single twitch, double-burst stimulation, train of four, tetanic stimulation and post tetanic count.

20. Electrical medical equipment as claimed in claim 19 wherein said double-burst stimulation is in the form of two sets of three rapid pulses, said sets separated by a pause of a set time interval controlled by said controller and user-adjustable via said controls, said time interval having a default value of 750 milliseconds.

21. Electrical medical equipment as claimed in claim 19 wherein said double-burst stimulation is in the form of a first set of two rapid pulses and a second set of three rapid pulses, said sets separated by a pause of a set time interval controlled by said controller and user-adjustable via said controls, said time interval having a default value of 750 milliseconds.

22. Electrical medical equipment as claimed in claim 19 wherein said double-burst stimulation is in the form of a first set of three rapid pulses and a second set of two rapid pulses, said sets separated by a pause of a set time interval controlled by said controller and user-adjustable via said controls, said time interval having a default value of 750 milliseconds.

23. Electrical medical equipment as claimed in claim 19 wherein said double-burst stimulation is in the form of a first set of a variable number of rapid pulses and a second set of a variable number of rapid pulses, separated by a pause of a variable time interval, said variable pulse numbers and said variable time interval programmed into said controller and user-adjustable via said controls.

24. Electrical medical equipment as claimed in claim 3 wherein said first position is a central position of said rocker switch, said rocker switch having at least one up position, and at least one down position, and wherein depressing said rocker switch into said electrical medical equipment corresponds to said fourth condition.

25. Electrical medical equipment as claimed in claim 1 wherein said primary adjustment mechanism is a rotating knob, said knob defaulting to said first condition when not manipulated by said user, and wherein rotating said knob in a first direction corresponds to said second condition, rotating said knob in a second direction corresponds to said third condition, and depressing said rotating knob corresponds to said fourth condition.

26. Electrical medical equipment as claimed in claim 25 wherein said distinct output varies depending on the angle or distance said knob is rotated away from said first condition, said controller receiving said variable distinct output as a variable input and responding by increasing or decreasing the prevailing level of said output parameter at a rate that corresponds to said angle or distance.

* * * * *

UNITED STATES PATENT AND TRADEMARK OFFICE
CERTIFICATE OF CORRECTION

PATENT NO. : 8,160,694 B2
APPLICATION NO. : 12/064900
DATED : April 17, 2012
INVENTOR(S) : Salmon et al.

Page 1 of 1

It is certified that error appears in the above-identified patent and that said Letters Patent is hereby corrected as shown below:

In column 3 at line 25-26, change "4 OmA and 5 OmA" to --40 mA and 50 mA--.

In column 4 at line 23, change "Life-tech." to --Life-tech,--.

In column 5 at line 28, change "damage" to --damage.--.

In column 6 at line 25, change "inc," to --Inc.,--.

In column 10 at line 11, change "preset" to --pre-set--.

In column 12 at line 5, change "preset" to --pre-set--.

In column 12 at line 19, change "preset" to --pre-set--.

In column 12 at line 36, change "in A." to --mA.--.

In column 15 at line 65, In Claim 9, change "all of" to --all of,--.

In column 16 at line 19, In Claim 11, after "as claimed" delete "in claimed".

Signed and Sealed this
Thirtieth Day of October, 2012

David J. Kappos
*Director of the United States Patent and Trademark Office*